United States Patent [19]

Schoetensack et al.

[11] 4,011,332
[45] Mar. 8, 1977

[54] HEMORRHAGIC-LESION PRODUCING AND ANTICOAGULANT-CONTAINING COMPOSITIONS AND THEIR USE

[75] Inventors: Wolfgang Schoetensack, Hegne; Richard Riedel, Constance, both of Germany

[73] Assignee: Byk Gulden Lomberg Chemische Fabrik GmbH, Germany

[22] Filed: Feb. 3, 1975

[21] Appl. No.: 546,765

[30] Foreign Application Priority Data

Feb. 20, 1974 Luxembourg .................. 69428

[52] U.S. Cl. .............. 424/273; 424/244; 424/263; 424/267; 424/270; 424/272; 424/275; 424/281; 424/285; 424/356

[51] Int. Cl.² ............ A61K 31/415; A61K 31/37; A61K 31/33

[58] Field of Search .......... 424/281, 273, 244, 263, 424/267, 270, 272, 275, 285, 356

[56] References Cited

UNITED STATES PATENTS 2,999,049  9/1961  Link .................. 424/281

FOREIGN PATENTS OR APPLICATIONS 37-16,750  1962  Japan .................. 424/281

OTHER PUBLICATIONS

Instituto – Chem. Abst., vol. 63 (1965) p. 7605h.

*Primary Examiner*—Sam Rosen
*Attorney, Agent, or Firm*—Berman, Aisenberg & Platt

[57] ABSTRACT

A combination of a physiologically-active component which produces hemorrhagic gut and/or stomach lesions and a physiologically-active component which inhibits blood clotting, ingested by a rodent either concurrently or in either sequence, provides an effective rodenticide.

22 Claims, No Drawings

HEMORRHAGIC-LESION PRODUCING AND ANTICOAGULANT-CONTAINING COMPOSITIONS AND THEIR USE

BACKGROUND OF THE INVENTION

Rats, e.g., have particularly good memories and a relatively high intelligence quotient. They are able to connect the toxic effect of rapidly-acting poisons with the type and position of employed bait, and they warn other rats.

Rodenticides comprising anti-coagulating or anti-clotting agent(s) have the advantage that hemorrhaging is produced several days after repeated administration and is thus not readily attributed by the rodents to the effect of the poison. Rodent corpses are not generally found about a feeding place so as to alarm other rats.

However, such rodenticides have a serious deficiency; the poison (anti-coagulant or anti-clotting agent) ordinarily fails to have lethal effect unless consumed in sufficient quantity a number of times (cumulative effect) by the same rodent. Experience has shown that this factor considerably reduces the success of anti-coagulant-based rodenticides for combatting and/or eliminating rodents.

Oral anticoagulants [cf., e.g., Goodman, Louis S., and Gilman, Alfred, "The Pharmacological Basis of Therapeutics" ; third edition, pages 1451 and 1452, The Macmillan Company, 1965] and hemorrhagic-lesion-producing drugs [cf., e.g., "Physicians' Desk Reference" ; 27th edition, pages 756 (right column) and 1000 (left column), 1973] are known.

SUMMARY OF THE INVENTION

Combining the action of a blood-clot inhibitor with that of a hemorrhagic-lesion-producer results in particularly-effective means for combatting rodents. The respective actions combine synergistically and produce a lethal effect when ingested by rodents.

There are a number of aspects to the subject invention which are directed to means for exterminating rodents and the use of such means to accomplish the desired result. Such aspects include:

A. Any combination of (a) component means to inhibit or prevent mammalian blood clotting with (b) component means to induce or produce hemorrhagic lesions in the alimentary canal;

B. Any admixture of component means enumerated under (A);

C. Any solid dosage form containing (A);

D. A rodenticide based on (A) in emetic-containing pellet form;

E. Inclusion in separate ingestible compositions of each of the component means enumerated under (A);

F. Rodent bait containing (A);

G. The use of (A) to combat or exterminate rodents; and

H. Placing a composition containing (A) at a location frequented by rodents.

The biological effects of component means (a) and component mens (b) [cf. under (A)] synergistically interact. The degree of synergism varies with the particular combinations of component means selected, but is most pronounced for those combinations wherein component means (b) is a carboxylic acid or a precursor which yields a carboxylic acid when contacted with gastric juice.

The lethal effect on rodents, such as rats and mice, of the combined ingestion of components (a) and (b) is assured. Hemorrhagic stomach and/or gut lesions produced by component (b) combine with induced inhibition of blood clotting to bring about death from hemorrhage in the gastrointestinal tract after a single ingestion. Rodenticides based on the combination of components (a) and (b) have a distinct advantage over many acutely-effective rodenticides, such as thiourea derivatives, phosphoric acid esters and heavy metal (organic or inorganic) compounds; they have a relatively low toxicity for man and for domestic animals, their toxic effects appear more slowly in man and in domestic animals and such toxic effects are limited by doses of vitamin K Furthermore the use of the new rodenticides takes into account the good memory and the high intelligence quota of the rat. In the case of rapidly acting poisons the rats are capable of connecting the toxic effect with the type and position of the bait and they warn other rats. Accordingly operations intended to destroy rats with such materials are often completely unsuccessful.

Previously used rodenticides comprising anti-coagulating or clotting agents have admittedly the advantage that after repeated administration of the anti-coagulants the haemorrhage produced only occurs after a few days and cannot be connected by the rats with the effect of the poison and the other rats are not alarmed by the corpses adjacent to the place of feeding, but, however, they have a serious disadvantage. The poison usually only acts lethally if it is consumed a number of times by the rat (cumulative effect). This reduces considerably, as experience has shown, the success of such pest destroying actions despite all of the advantages which are offered by materials which prevent clotting of the blood.

The novel rodenticide has, as compared with the use of a known rodenticide comprising as an active substance anticlotting materials alone, the advantage that even a single consumption of the poison by the rat acts lethally, but the lethal effect only occurs a few days after consumption. Thus the animals cannot recognize any connection between the poison and the effect. In addition the novel rodenticide combined with any bait has the advantage to be well accepted by rodents, e.g. rats, thus strengthening the consumption of the poison and the lethal effect of the inventive combination. The new combination of active substances therefore fulfils all conditions for a reliable rodenticide.

The danger of poisoning persons or domestic animals is substantially avoided, e.g., by providing the rodenticide in pellet form, each pellet having a core [containing the combination of active components (a) and (b)] in a casing which is soluble in intestinal juice (basic fluid), but is not soluble in gastric juice (acidic). Such casing is further coated with an emetic-comprising layer and an outermost layer (tasteless, insoluble in saliva, but soluble in gastric juice). When a person or a domestic animal ingests the pellet, the outermost layer dissolves in gastric juice and the emetic performs its function to induce vomitting. Rats and mice are incapable of vomitting.

DETAILS

Compositions are provided with two essential components: a) active substance which, upon ingestion (oral administration), inhibits blood clotting in or prolongs clotting time for mammals, e.g. rodents, such as rats and mice, and b) active substance which produces hemorrhagic lesions in the alimentary canal, e.g. the stomach and/or gut, of mammals, particularly rodents, by which it has been ingested.

The compositions, which produce specific effects by cooperation or synergism between the two components, advantageously comprise from 5 to 95 percent of component (a) and from 95 to 5 percent of component (b), expressed as percentages by weight of the composition as a whole. Compositions having from 20 to 90 percent by weight of component (a) and from 80 to 10 percent by weight of component (b) are preferred. Compositions with from 35 to 75 percent by weight of component (a) and from 65 to 25 percent by weight of component (b) are particularly useful.

The compositions can, but need not necessarily, consist exclusively of components (a) and (b). The compositions, however, optionally have any total content of components (a) and (b) which is at least $10^{-3}$ percent by weight. Compositions with a total content of components (a) and (b) of more than $10^{-3}$ percent by weight are advantageously employed, and those with a total content of components (a) and (b) in excess of $10^{-2}$ percent by weight are preferred. The amounts or proportions of the individual components (a) and (b) are readily calculated from the preceding data. The ratio of the two components to each other, that is the respective amounts of components (a) and (b), is selected by those skilled in the art in accord with accepted criteria, including economic aspects. The cheaper component is used in excess whenever appropriate. The compositions optionally comprise further active substances as well as adjuvants.

The compositions are ordinarily produced in solid form. In such form they consist either exclusively of the two active substances or comprise the active substances in the previously-mentioned relative concentrations together with further active substances, solid adjuvants, inert filler and/or carrier.

Solid compositions exist, for example, in the form of spheroidal particles, in powder or pellet form, in the form of a granulate, as a granular material, in the form of particles coated with a film or in the form of a stiff paste.

Solid compositions are preferably compounded so that the two active substances are distributed in them in the desired weight ratio with the most even concentration possible.

The compositions, are, alternatively, in a liquid form (for example, dissolved in a suitable solvent) or in a suspended form (for example, suspended in water, a mineral oil, seed oil or honey).

Component (a) includes any one or combination of orally-effective anti-coagulants or anti-clotting agents which, e.g., interfere with prothrombin synthesis and-/or block prothrombin circulating in the blood of mammals.

Examples of component (a) include, but are not limited to, derivatives of 1,3-indandione, derivatives of coumarin, 2-azacycloalkylmethyl-substituted benzhydrylketones and -carbinols and salts of rare earth metals, particularly of neodymium and cerium.

Preferred 1,3-indandiones are: 2-($\beta$-methylbutyryl)-1,3-indandione [cf. J. Organ. Chem., 25, 1869 (1962)], 2-phenyl-1,3-indandione [Chem. Ber. 47, 1439 (1914)], 2-(p-chlorphenyl)1,3-indandione (British patent No. 748,251), 2-($\alpha,\alpha,\alpha$-trifluoro-p-tolyl)-1,3-indandione (Dutch Octrooischrift No. 65, 11, 171), 2-(p-bromophenyl)-1,3-indandione (U.S. Pat. No. 2,847,747), 1-(p-methoxyphenyl)-1,3-indandione (U.S. Pat. No. 2,899,358), 2-(diphenylacetyl)-1,3-indandione (U.S. Pat. No. 2,672,483), 2-[1-(p-bromophenyl)-1-phenyl]acetyl-1,3-indandione (French Pat. No. 1,269,638), 2-[1-(p-tolyl)-1-phenyl]acetyl-1,3-indandione (Russian Pat. No. 145,417), 2-phenyl-2-morpholinomethyl-1,3-indandione (German Pat. No. 1,919,895), 2-hydroxymethyl-2-phenyl-1,3-indandione [Comp. Rend., 257(4), 933–6 (1963)], 2-(1-naphthyl)-1,3-indandione (French Pat. No. 1,085,097), 2-($\alpha$-(p-ethylphenacetyl)benzyl]-1,3-indandione [Zh. Obshch. Khim., 35(1), 184–5 (1965)] and 2-pivaloyl-1,3-indandione [Ind. Eng. Chem., 34, 494–7 (1941)] and their salts.

Preferred anti-clotting agents or anticoagulants based on coumarin are: 4-hydroxy-2-oxo-3-(1-phenylpropyl)-2H-chromene (U.S. Pat. No. 2,723,276), 4-hydroxy-2-oxo-3-(3-oxo-1-phenylbutyl)-2H-chromene (U.S. Pat. No. 2,427,578) and its sodium salt (U.S. Pat. No. 2,765,321), 4-hydroxy-2-oxo-3-[3-oxo-1-(p-chlorophenyl)butyl]-21 H-chromene (U.S. Pat. No. 2,648,682), 2-methoxy-5-oxo-2-methyl-4-phenyl-3,4-dihydro-2H,5H-pyrano[3,2-c] [1]benzopyrane [cf. J. Am. Chem. Soc., 66, 902–6 (1944)], 4-hydroxy-2-oxo-3-[4-hydroxy-2-oxo-2H-chromenyl-(3)-methyl]-2H-chromene [Arquiv. inst. biol. (sao Paulo), 14, 293–303 (1943)], 4-hydroxy-21 -oxo-3-{1-[4-hydroxy-2-oxo-2H-chrome nyl-(3-]-ethyl}-2H-chromene (Czech. Pat. No. 85,918), 4-hydroxy-2-oxo-3-{2-methoxy-1-[4-hydroxy-2-oxo-2H-chromenyl-(3)]-ethyl}-2H-chromene [Rec. Trav. Chim. 72, 358-364 (1953)], 4-hydroxy-2-oxo-3-{3-methylmercapto-1-[4-hydroxy-2-oxo-2H-chromenyl-(3)]-pyropyl}-2H-chromene [Proc. Intern. Conf. Thrombosis and Embolism, 1st, Basle, 1954, 223-7 (published 1955)], ethyl-bis-[4-hydroxy-2-oxo-2H-chromenyl-(3)]-acetate (U.S. Pat. No. 2,482,510), 3-(1,2,3,4-tetrahydro-1 naphthyl)-4-oxycoumarin (German Pat. No. 1,014,551), 3-[$\alpha$-(2-furyl)-$\beta$-acetylethyl]-4-oxycoumarin (German Pat. No. 947,164), 4-hydroxycoumarin-3-carboxylic acid-$\beta$-diethylaminoethylamide (French Pat. No. 1,369,991), 4-hydroxy-3-(3,5-xylyl)coumarin [Sci. Communs. Research Dept., N.V. Koninkl. Pharm. Fabrieken v/h Brocades-Stheeman & Pharmacia, 10, 7–78 (1960–1961)], 3-]1-(p-chlorophenyl)propyl]-4-hydroxycoumarin (British Pat. No. 734,823), 3-(1-naphthyl)-4-hydroxycoumarin (U.S. Pat. No. 2,723,276), 3-[1-(p-iodophenyl)-3-oxobutyl]-4-hydroxycoumarin (Belgian Pat. No. 626,118), 4-hydroxy-3-[1-(p-nitrophenyl)-3-oxopentyl]coumarin (U.S. Pat. No. 2,648,682) and 4-hydroxy-3-(3-oxo-1-phenylpentyl)coumarin [Izv. Vysshikh Uchebn. Zavedenii, Khim. Tekhnol., 5(1), 107–111 (1962).].

Further anti-clotting agents include the following 2-azacycloalklmethyl-substituted benzhydrylketones and -carbinols: 1-phenyl-3-(2-piperidyl)-1-(p-tolyl)-2-propanone; 3,3-diphenyl-1-(2-pyrrolidinyl)-2-pentanone; 1,1-diphenyl-3-[2-(hexahydro-1H-azepinyl)]-2-propanone; 1-(4-fluorophenyl)-1-phenyl-3-(2-piperidyl)-2-propanone; 1-(4-methylthiophenyl)-1-phenyl-3-(5,5-dimethyl-2-pyrrolidinyl)-2-propanone; 1-(p-coumenyl)-1-phenyl-3-(4-tert. -butyl-2-piperidinyl)-2-propanone; 3,3-diphenyl-1-[2-(hexahydro-1H-azepinyl)]-2-butanone; 3-(2,4-dichlorophenyl)-3-phenyl-1-(2-piperidyl)-2-heptanone; 1,1-diphenyl-3-(5-methyl-2-pyrrolidinyl)-2-propanone;

3,3-diphenyl-1-(2-piperidyl)-2-butanone; α-(α-methyl-α-phenylbenzyl)-2-piperidinethanol; α-(α-ethyl-α-phenylbenzyl)-2-pyrrolidinethanol; 2-(2,5-dimethyl-α-phenylbenzyl)-2-piperidinethanol and α-(diphenylmethyl)-2-(hexahydro-1H-azepin)ethanol and their salts, which are described in the German patent specification 2,417,783, and 4'-(fluorophenyl)-2-(2-pyrrolidinyl)acetophenone, 4'-phenyl-2-(5,5-dimethyl-2-pyrrolidinyl)acetophenone, 4'[p-(trifluoromethyl)-phenyl]-2-(2-piperidyl)acetophenone, 4'-(p-butoxyphenyl)-2-(4-tert.-butyl-2-piperidyl)acetophenone, 2'-phenoxy-2-(2-piperidyl)acetophenone, 4'-(p-fluorophenoxy)-2-(5,5-dimethyl-2-pyrrolidinyl)acetophenone, 4'-(p-chlorophenoxy)-2-(2-piperidyl)acetophenone, 4'-[m-(trifluoromethyl)phenoxy[-2-(2-piperidyl)acetophenone, 4'-(p-butoxyphenoxy)-2-(2-pyrrolidinyl)acetophenone, 2-(2-piperidyl)-4'-(trans-p-tolylvinylene)acetophenone, 2-(2-hexahydro-1H-acepinyl)-4'-(trans-styryl)acetophenone, 4'-(m-methoxyphenylvinylene)-2-(2-pyrrolidinyl)acetophenone, 2-(2-piperidyl)-4'-[(p-methylthio)phenylvinylene]acetophenone, 4'-(3-phenoxypropoxy)-2-(2-piperidyl)acetophenone, 4'-(4-phenylbutyl)-2-(2-piperidyl) acetophenone, 4'-(α,α-dimethylbenzyl)-2-(piperidyl)acetophenone, 4'-phenethyl-2-(3,5-diethyl-2-piperidyl)acetophenone, 4'-phenyl-2-(2-pyrrolidinyl)acetophenone, α-[2-(2-phenylethoxy)-phenyl]-2-piperidinethanol, α-(p-phenoxyphenyl-2-pyrrolidinethanol, α-[4-(4-bromophenoxy)phenyl]-6-methyl-2-piperidinethanol, α-(p-phenethyl)phenyl-2-pyrrolidinethanol, α-(p-biphenyl)-2-hexahydro-1H-azepinethanol, α-[3-(4-phenoxybutoxy)phenyl]-2-piperidinethanol, and α-(4-benzyl)phenyl-2-piperidinethanol and their salts, which are described in German Pat. No. 2,418,480.

The following rare earth metal salts are, alternatively, used as anti-clotting agents: dineodymiumdihydroxybenzene disulfonate (Acta physiol. Acad. Sci. Hungar., 24, 373), dineodymium-3-sulfonate-pyridine-carboxylate-(4) and cerium-(III)-tris-(4-aminobenzene sulfonate).

As part of the invention preference is accorded anticlotting agents which are known to be rodenticidally-active materials and are readily available commercially.

The second active component (b) is one which causes hemorrhagic stomach and/or gut lesions when it is orally administered (on an empty stomach) alone in a single dose of less than 50 mg/kg of body weight to Sprague-Dawley rats. Component (b) is preferably so selected that it causes hemorrhagic stomach and/or gut lesions after a single oral administration (on an empty stomach) of less than 15 mg/kg of body weight of Sprague-Dawley rats.

In cooperation with component (a) those components (b) which cause hemorrhagic stomach and/or gut lesions in rats when orally administered (on an empty stomach) once in a dose of less than 5 mg/kg of body weight produce pronounced desired effects in the subject compositions.

The method described by K. P. Bhargava, M. B. Gupta and K. K. Tangri in European J. Pharmacol., 22, 191–195, 1973, is, e.g., used to determine gut lesions.

A selection of compounds from those suitable for component (b) is, however, made in a simpler manner by determining the $LD_5$ (in mg/kg). The respective dose of a substance is that which, after being administered, causes 5% (= $LD_5$; determination in accord with J. T. Litchfield and F. Wilcoxon in J. Pharmacol. exp., 96, 99, 1949) of the treated animals to die owing to massive hemorrhagic stomach and/or gut lesions, that is perforation of the gastrointestinal tract. Determination of the cause of death is effected, e.g., by autopsy of the dead animals.

For testing, Sprague-Dawley rats of both sexes, each weighing from 150 to 250 g, were fed on commercially-available standard food and water ad lib. The rats were kept in groups of 5 and four animals in plastic cages of the type M III. The room temperature was maintained at approximately 23° C. For determining the lethal doses, as mentioned in the following description, the rats were fed on empty stomachs. The animals received the noted compounds [for example, component (a) or (b) or the composition containing both] in a volume of liquid amounting to 5 ml per kg of body weight of the rat. The administration of the liquid was carried out once using a feeding tube introduced into the oesophagus. The doses of the active substances [component (a), component (b) or the composition] were varied. Component (b) was administered as a sodium salt in aqueous solution, and the number of animals which died within 10 days after administration was noted.

The lethal doses ($LD_5$, $LD_{50}$ and $LD_{100}$ in mg/kg) were determined by simple linear regression, while the limits of trust were determined by the method of Litchfield and Wilcoxon.

In the investigation of stomach and/or gut lesions and in the determination of lethal doses, more particularly $LD_5$, it is advisable to use a rat strain whose $LD_5$ for 4-butyl-1,2-diphenyl-3,5-pyrazolidinedione (= phenylbutazone) amounts to 600 mg/kg of body weight of the rat and whose $LD_5$ for 1-(p-chlorobenzoyl)-5-methoxy-2-methylindole-3-acetic acid (= indometacine) amounts to approximately 7 mg/kg of body weight of the rat.

With these convenient selection criteria for determining stomach and/or gut lesions and $LD_5$, acidic aromatic compounds with a molecular weight of from approximately 200 to approximately 500 [with 1 to 5 rings, 6 to 30 carbon atoms and a $pK_A$-value of 1.5 to 5.5 and, more particularly, approximately 2 to 5 (extrapolated { log $pK_A$ in a dilution series extrapolated to a solution with pure water as a solvent} or converted {J. Am. Chem. Soc., 87, 5275 (1965)} to apply for an aqueous medium were found to constitute excellent representatives of component (b).

Among these acidic compounds those which are particularly noteworthy are:
a. carboxylic acids
b. enols
c. NH-acidic compounds
d. salts or derivatives of compounds (a) to (c) which, in the pH range of gastric juice of mammals, are convertible to release the acid compound.

The (carboxylic acid) components (b) are characterized by the carboxylic acid radical which has from 1 to 4 carbon atoms and is directly bound to a carbocyclic or heterocyclic aromatic ring.

The (acidic enol) components (b) are characterized by the system

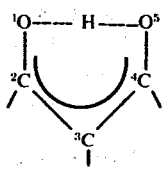

containing 5 atoms. Particularly suitable representatives are those wherein carbon atoms 2, 3 and 4 form components of further conjugated systems.

The components (b) (on the basis of NH-acidic compounds) are characterized by groups, such as the —NHSO$_2$CHF$_2$ or the —NHSO$_2$CF$_3$ group. The pK$_A$-values of these compounds lie between approximately 2 and approximately 5.

Preferred aromatic carboxylic acid and enol compounds (b) are compounds which comprise from 9 to 25 carbon atoms. The carbon atom skeleton of preferred carboxylic acid radicals bound to aromatic nuclei comprises 1, 2 or 3, and more particularly 2, carbon atoms. Only those carboxylic acids with a C=O bond (in the carboxylic acid radical) separated by at least two C—C bonds from the closest C=C bond [i.e., with a C=O bond which is not in conjugation with a double bond] are encompassed by one aspect of the subject invention.

Representative of the preferred component (b) are arylacetic acids, α-aryl-α-methylacetic acids and arylpropionic acids.

The aryl radical bound to the carboxylic acid radical is either carbocyclic (abreviated as Ar in what follows), preferably comprising from 6 to 20 ring carbon atoms (abreviation: Ar$^1$), or heterocyclic (abreviation: Het), preferably comprising from 1 to 20 ring carbon atoms (abreviation: Het$^1$) and, most advantageously, having from 3 to 15 ring carbon atoms.

Preferred Het$^1$ radicals comprise 1 or 2 nitrogen atoms, 1 oxygen atom, 1 sulfur atom, 1 nitrogen atom and 1 oxygen atom, or 1 nitrogen and 1 sulfur atom in the ring.

Excellent representatives of component (b) are arylcarboxylic acids which comprise monocylic radical Ar$^1$ or Het$^1$ bound to the carboxylic acid radical. An example of such a radical Ar$^1$ is the phenyl radical. Examples of such a Het$^1$ radical are the pyrrolyl, thienyl, furyl, pyrazolyl, thiazolyl, pyridyl and the oxazolyl radicals. In many cases these radicals (Ar$^1$ or Het$^1$) carry further substituents, for example 1 to 3 lower alkyl radicals and/or lower alkoxy radicals and/or an alkanoyl radical with up to 12 carbon atoms and/or an aroyl radical with up to 12 carbon atoms and/or a nitro group and/or 1 to 3 halogen atoms and, more particularly, 1 to 3 fluorine, chlorine or bromine atoms.

Further excellent representatives are compounds with a condensed Ar$^1$ or Het$^1$ radical which has at least 2 rings with at least two atoms in common. Examples for condensed Ar$^1$ radicals are the naphthyl, the indenyl, the anthryl, the acenaphthyl, the fluorenyl, the indanyl and the biphenylenyl radicals. Examples for condensed Het$^1$ radicals are the benz[b]-thiophenyl, the thioxanthenyl, the phenoxathiinyl, the indolizinyl, the indolyl, the 2H-isoindolinyl, the indazolyl, the carbazolyl, the phenothiazinyl and the benzoxazolyl radicals. In many cases these condensed Ar$^1$ or Het$^1$ radicals carry further substituents, for example 1 to 3 lower alkyl radicals and/or lower alkoxy radicals and/or an alkanoyl radical with up to 12 carbon atoms and/or 1 to 3 halogen atoms, more particularly 1 to 3 fluorine, chlorine or bromine atoms and/or n aroyl radical with up to 12 carbon atoms and/or a nitro group.

In addition to the Ar$^1$ or Het$^1$ radical bound to the carboxylic acid radical some representatives comprise further saturated or unsaturated isocyclic or heterocyclic rings. Examples of saturated isocyclic radicals are the cyclohexyl, cyclopentyl, cycloheptyl and the cyclopropyl radicals. Examples of unsaturated isocyclic radicals are the phenyl, cyclohexenyl, cyclopentenyl and the naphthyl radicals. Examples of saturated heterocyclic radicals are the piperidyl and pyrrolidinyl radicals. Examples of unsaturated heterocyclic radicals are the pyrrolinyl, pyrrolyl, thienyl, furyl, thiazolyl, oxazolyl, isoxazolyl, pyridyl, benzthiazolyl and benzoxazolyl radicals.

Therefore, further excellent representatives of component (b) are carbocyclic or heterocyclic arylcarboxylic acids, whose Ar$^1$ or Het$^1$ radical bound to the carboxylic acid radical is linked with one or more (up to 4) rings directly by simple bonds to form a ring assembly in accordance with IUPAC Rule A-51. Such a ring assembly comprises 4 to 26 carbon atoms, including the carbon atoms of the substituents. These ring assemblies are (in what follows) denoted as R$_a$. The R$_a$ radical is termed carbocyclic or heterocyclic aromatic if it comprises an Ar$^1$ or a Het$^1$ radical, that is to say if the carboxylic acid radical is linked with the carbocyclic or heterocyclic aromatic radical. Examples of unsubstituted carbocyclic aromatic R$_a$ radicals are the 4-cyclohexylphenyl, the 4-biphenylyl, the 3-biphenylyl, the 5-cyclohexyl-1-indanyl, the 4-(1-cyclohexen-1-yl)phenyl, the 4-(3-pyrrolin-1-yl)phenyl, the 4-(1-piperidyl)phenyl, the 4-(2-thienyl)phenyl and the 5-phenyl-1-naphthyl radicals.

Examples of heterocyclic aromatic R$_a$ radicals are the 1,3,5-triphenyl-4-pyrazolyl, the 1-phenyl-3,5-di(2-thienyl)-4-pyrazolyl, the 2,4,5-triphenyl-3-thienyl, the 1,3,4-triphenyl-5-pyrazolyl, the 2,4-diphenyl-5-thiazolyl, the 2-phenyl-4-(2-thienyl)-5-thiazolyl and the 3-cyclohexyl-1,5-diphenyl-4-pyrazolyl radicals.

In many cases the R$_a$ radicals carry from 1 to 3 substituents, for example 1 to 3 lower alkyl and/or alkoxy radicals and/or 1 to 3 halogen atoms are more particularly 1 to 3 fluorine, chlorine or bromine atoms and/or an alkanoyl radical with up to 12 carbon atoms and/or an aroyl radical with up to 12 carbon atoms and/or a nitro group.

Examples for substituted R$_a$ radicals are the 1,3-diphenyl-5-(p-methoxyphenyl)-4-pyrazolyl, the 3,5-diphenyl-1-(p-methoxyphenyl)-4-pyrazolyl and the 3-(p-chlorophenyl)-1,5-diphenyl-4-pyrazolyl radicals.

Examples of components (b) which, in the compositions, provide the strongest synergistic action are:

1-(p-chlorobenzoyl)-5-methoxy-2-methylindole-3-acetic acid and its salts
3-chloro-4-cyclohexyl-α-methylphenylacetic acid, preferably its d(+) isomer and its salts
1,3,5-triphenyl-4-pyrazole acetic acid and its salts
1,3,4-triphenyl-5-pyrazole acetic acid and its salts
1-phenyl-3,5-di-(2-thienyl)-4-pyrazole acetic acid and its salts
1-(p-chlorophenyl)3,5-di-(2-thienyl)-4-pyrazole acetic acid and its salts 1,5-diphenyl-3-(p-chlorophenyl)-4-pyrazole acetic acid and its salts
3-cyclohexyl-1,5-diphenyl-4-pyrazole acetic acid and its salts
1,3-diphenyl-5-(p-methoxyphenyl)-4-pyrazole acetic acid and its salts
3,5-diphenyl-1-(p-methoxyphenyl)-4-pyrazole acetic acid and its salts
6-chloro-5-cyclohexylindan-1-carboxylic acid, preferably its (1S)-(+)-isomer and its salts
β-(3-chloro-4-cyclohexylphenyl)-β-methylpropionic acid and its salts
2-chloro-4'-fluoro-α-methyl-4-biphenylacetic acid and its salts
2-chloro-2',4'-difluoro-α-methyl-4-biphenylacetic acid and its salts
2,2',4'-trifluoro-α-methyl-4-biphenylacetic acid and its salts
2-[4-(1-oxo-2-isoindolinyl)phenyl]propionic acid and its salts
d(+)-2-(5-phenyl-1-naphthyl)propionic acid and its salts
2-(2-fluorenyl)propionic acid and its salts
1-(p-chlorobenzylidene)-2-methyl-5-methoxyindene-3-acetic acid and its salts
5-(p-chlorobenzoyl)-1,4,α-trimethylpyrrol-2-acetic acid and its salts
5-(p-fluorobenzoyl)-1,4-dimethylpyrrol-2-acetic acid and its salts
0-(2,6-dichloroanilino)phenylacetic acid and its salts
2-(5h-[1]benzopyrano[2,3-b]pyridin-7-yl)propionic acid and its salts The following acidic enol compounds are particularly significant as component (b):

N-(2-thiazolyl)-4-hydroxy-2-methyl-2H-1,2-benzthiazine-3-carboxamide-1,1-dioxide
N-(4-methyl-2-thiazolyl)-4-hydroxy-2-methyl-2H-1,2-benzthiazine-3-carboxamide-1,1-dioxide
N-(4,5-dimethyl-2-thiazolyl)-4-hydroxy-2-methyl-2H-1,2-benzthiazine-3-carboxamide-1,1-dioxide
N-(2-benzthiazolyl)-4-hydroxy-2-methyl-2H-1,2-benzthiazine-3-carboxamide-1,1-dioxide
N-(2-pyridyl)-4-hydroxy-2-methyl-2H-1,2-benzthiazine-3-carboxamide-1,1-dioxide
N-(6-methyl-2-pyridyl)-4-hydroxy-2-methyl-2H-1,2-benzthiazine-3-carboxamide-1,1-dioxide The following carboxamides (b) are alternatively formulated in keto-form:

N-(2-thiazolyl)-3-hydroxy-2-methyl-2H-1,2-benzthiazine-4-carboxamide-1,1-dioxide
N-(4-bromophenyl)-3-hydroxy-2-methyl-2H-1,2-benzthiazine-4-carboxamide-1,1-dioxide
N-(4-nitrophenyl)-3-hydroxy-2-methyl-2H-1,2-benzthiazine-4-carboxamide-1,1-dioxide
N-(2-methyl-4-nitrophenyl)-3-hydroxy-2-methyl-2H-1,2-benzthiazine-4-carboxamide-1,1-dioxide
1-methyl-2',4'-difluoroxindole-3-carboxanilide All noted examples of component (b) are produced, e.g., in accordance with methods described in the literature (see, inter alia, U.S. Pat. No. 3,161,654, Dutch Octrooischrift No. 6,608,311, German Offenlegungsschrift No. 2,123,705, Dutch Octrooischrift No. 7,016,787, Belgian Pat. No. 796,465, Greek Pat. No. 41,535, J. Med. Chem., 15, 1297–1306 (1972), Angew. Chem., 84, 512–526 (1972), South African Pat. No. 7201706, Belgian Pat. No. 704,182, J. Med. Chem., 16, 490–493 (1973), German Offenlegungsschrift No. 2,143,600, Belgian Pat. No. 633,314, J. Med. Chem., 16, 172–174 (1973), J. Med. Chem., 16, 493–96 (1973), J. Med. Chem., 14, 973–977 (1971), Compt. Rend., Ser. D. 273, 911 (1971), J. Med. Chem., 16, 131–134 (1973), Belgian Pat. No. 802,258, Dutch Octrooischrift No. 6,604,752.

Further components (b) are readily found on the basis of specified selection criteria and with the help of the investigation methods described by those in the art without departing from the teachings of this disclosure.

DEFINITIONS

In the preceding description, throughout the following text and in the appended claims terms are used according to their generally-accepted meanings. For ultimate clarification, however, some of these terms are specifically defined:

aromatic — unless otherwise specifically limited, this term encompasses both carbocyclic and heterocyclic aromatic groups, i.e. rings, radicals or entire compounds, according to the relevant text;

aryl — unless otherwise limited, a carbocyclic or heterocyclic monovalent radical;

cycloalkyl — a saturated monovalent carbocyclic radical having from 3 to about 8 ring carbon atoms;

derivative — N-aryl substituted 4-hydroxy-2-methyl-2H-1,2-benzothiazine-3-carboxamide-1,1-dioxides, preferably having a 2-thiazolyl-, 4-methyl-2-thiazolyl,4,5-dimethyl-2-thiazolyl-, 2-benzthiazolyl-, 2-pyridyl- or 6-methyl-2-pyridyl substituent and N-aryl substituted 3-hydroxy-2-methyl-2H-1,2-benzothiazine-4-carboxamide-1,1-dioxides, preferably having a 2-thiazolyl-, 4-bromophenyl-, 4-nitrophenyl- or 2-methyl-4-nitrophenyl substitutent.

hemorrhagic lesions — throughout the disclosure reference is to such lesions brought about in the gastrointestinal tract (unless otherwise defined) by ingestion of component means (b);

lower — having a carbon content of from 1 to 4 carbon atoms, used in conjunction with such terms as "alkyl" and "alkoxy";

precursor — limited to an immediate progenitor in the defined milieu;

salt — a compound of the corresponding acid with an inorganic or organic base which is derived from ammonia or from alkali metals, e.g. lithium, potassium, sodium, preferred is sodium, or from alkaline-earth metls, e.g. magnesium, calcium, strontium, arium, preferred is magnesium and barium, or from metals of group III a of the periodical system, e.g. aluminium, thallium, preferred is thallium, or from metals of group IV a of the periodical system, preferred is tin and lead, or from heavy metals, e.g. chromium, cobalt, copper, nickel, cadmium, iron, zinc, preferred is copper, iron and zinc, or from aliphatic or aromatic amines, e.g. ethylamine, triethylamine, ethanolamine, diethanolamine, ethylendiamine, benzylamine, pyrrolidine, piperidine, piperazine, morpholine, 1-ethyl-piperidine, preferred is ethylendiamine and triethylamine.

BIOLOGICAL PROPERTIES

The compositions have outstanding biological properties. Even a single small dose of one of the compositions (ingested by a rodent) causes hemorrhagic ulcers and perforations (in the stomach and/or on the mucous membrane of the gut) which lead to the death of the host animal from internal bleeding. Accordingly, the compositions are useful to combat (eradicate) and control (reduce the population of) harmful rodents, such as rats and field mice; they are rodenticides.

The compositions not only have a high efficacy against domesticated rats (Sprague-Dawley rats), but also with respect to wild rats (for example *Rattus rattus*, *Rattus norvegicus*, (*Rattus alexandrinus*), and they are also effective against *Mus musculus*, *Bandicota bengalensis*, Geomys spp., Thomamys spp., Citellus spp., and others.

The combination of active substances is useful as a rodenticide; it is supplied once or several times at suitable locations accessible to rodents for which it is intended. It is so provided in any ingestible form, including separate compositions or applied to or admixed with bait.

The subject rodenticide, as compared with known rodenticide comprising anti-clotting material, has the advantage that even a single ingestion of the poison by a rat acts lethally, but the lethal effect does not occur until a few days after consumption. Thus the animals fail to connect the poison with the effect. The new combination of active substances therefore fulfils all conditions for a reliable rodenticide.

PREPARATION AND APPLICATON

The composition is, e.g., prepared for sale as a concentrate which, prior to use, is diluted with any suitable adjuvant(s). The lethal effects of the novel composition of matter, however, occur even when a material, suitable for oral consumption, comprises from $10^{-3}$ to $10^{-2}$ percent by weight of component (a) and component (b), i.e. when 1 g of the material provided for oral consumption comprises from 0.01 to 0.1 mg of the novel composition of matter. With concentrations of up to $10^{-2}$ percent by weight, however, many of the subject compositions become effective only after repeated consumption by a rodent. A satisfying rodenticidal effect is achieved, if e.g. the novel composition of matter brings about a rate of mortality from 5 to 100 % after a single uptake, i.e. if the bait, which will be consumed by a rat during one feed, contains an amount of the novel composition of matter corresponding to $LD_5$ to $LD_{100}$ (expressed in mg/kg). Taking into consideration that a rat of 200 g of weight consumes during one feed about 0.8 g bait, i.e. that about 4g bait per kg body weight of rat will be taken up, and taking into account that young rats consume more feed per kg body weight than larger animals it follows that 1 g of the solid bait comprises the novel composition of matter in an amount (expressed in mg) of $$\frac{LD_5 \ldots LD_{100}}{10 \ldots 2} [mg].$$

$LD_5 \ldots LD_{100}$ have to be taken as absolute values of the lethal dosage (expressed in mg/kg) of the combination of active substances.

The factor 2 ... 10 in the denominator takes into consideration the fact that the concentration of the active substance in the bait is optionally adapted to the variable weight and age of the rodents, e.g. young rats have a body weight of 100 g, the largest rats rach a weight of approximately 500 g.

A reliable rodenticidal effect is achieved when, e.g., the novel composition of matter brings about a rate of mortality from 50 to 100 % after a single uptake, i.e., if 1 g of solid bait contains the novel composition of matter in an amount (expressed in mg) of preferably $$\frac{LD_{50} \ldots LD_{100}}{10 \ldots 2} [mg].$$

An excellent rodenticidal effect is achieved if, e.g., the novel composition of matter brings about a rate of mortality from 90 to 100 % after a single uptake, i.e. when 1 g solid bait contains, in a preferred embodiment of the invention, the novel composition of matter in an amount (expressed in mg) of $$\frac{LD_{90} \ldots LD_{100}}{10 \ldots 2} [mg].$$

When the novel composition is in a form suitable for application, for example as bait, the total content of this form of components (a) and (b), is generally from $10^{-3}$ to 5, and preferably from approximately $10^{-2}$ to 1, percent by weight. The amounts of individual components (a) and (b) are calculated from previously-provided data. It is convenient for both components to be present in aproximately equal amounts by weight for particularly-effective compositions.

Components (a) and (b) are present in the novel compositions, for example, as a more or less homogeneous mixture, as a solution or suspension or emulsion, or as separate components.

Preferred rodenticidal compositions of matter are specified in Table I.

The two components (a) and (b), are preferably combined together to form a lethal dose, which can be directly laid, mixed with adjuvants or further processed to produce a bait. They can be applied to or admixed with food material for the animal (host) to be poisoned or applied to a bait. The two components are, e.g., spread in the form of a powder on food or bait for the animal or, as an alternative, the food or bait for the animal can be impregnated with a solution, suspension or emulsion of the two components.

The two components are, alternatively, made accessible to the animals at different times and in any suitable sequence; the component causing hemorrhagic lesions can be ingested either prior to, concurrently with or subsequent to that which inhibits blood clotting. Sequential ingestion, however, involves the disadvantage of requiring animals to consume the composition more than once.

The invention also relates to a method for combatting harmful rodents, more particularly rats and field mice, by administering to them a lethal dose of (a) an active substance which hinders or prevents clotting of the blood and (b) an active substance

Table I

*Preferred Rodenticides*
Component (a) combined with component (b).

| No. | Component (a) | No. | Component (b) |
|---|---|---|---|
| 1.1 | 4-hydroxy-2-oxo-3-(1-phenyl-propyl)-2H-chromene | 2.1 | 1,5-diphenyl-3-(p-chlorophenyl)-4-pyrazole acetic acid or a salt thereof |
| 1.2 | 4-hydroxy-2-oxo-3-(3-oxo-1-phenylbutyl)-2H-chromene | 2.1 | " |
| 1.3 | 2-diphenylacetyl-1,3-indandione | 2.1 | " |
| 1.4 | 2-pivaloyl-1,3-indandione | 2.1 | " |
| 1.5 | 2-(4-chlorophenyl)-1,3-indandione | 2.1 | " |
| 1.6 | 4-hydroxy-2-oxo-3-[3-oxo-1-(4-nitrophenyl)butyl]-2H-chromene | 2.1 | " |
| 1.7 | 3-(1,2,3,4-tetrahydro-1-naphthyl)-4-hydroxycoumarin | 2.1 | " |
| each of 1.1 to 1.7 individually or in any combination | | 2.2 | 1,3,4-triphenyl-5-pyrazole acetic acid |
| each of 1.1 to 1.7 individually or in any combination | | 2.3 | 1-phenyl-3,5-di-(2-thienyl)-4-pyrazole acetic acid or a salt thereof |
| each of 1.1 to 1.7 individually or in any combination | | 2.4 | 1,3,5-triphenyl-4-pyrazole acetic acid or a salt thereof |
| each of 1.1 to 1.7 individually or in any combination | | 2.5 | 1-p-chlorophenyl-3,5-di-(2-thienyl)-4-pyrazole acetic acid or a salt thereof |
| each of 1.1 to 1.7 individually or in any combination | | 2.6 | 1-(p-chlorobenzoyl)-5-methoxy-2-methylindole-3-acetic acid or a salt thereof |
| each of 1.1 to 1.7 individually or in any combination | | 2.7 | 3-cyclohexyl-1,5-diphenyl-4-pyrazole acetic acid or a salt thereof |
| each of 1.1 to 1.7 individually or in any combination | | 2.8 | 1,3-diphenyl-5-(p-methoxyphenyl)-4-pyrazole acetic acid or a salt thereof |
| each of 1.1 to 1.7 individually or in any combination | | 2.9 | 3,5-diphenyl-1-(p-methoxyphenyl)-4-pyrazole acetic acid or a salt thereof |
| each of 1.1 to 1.7 individually or in any combination | | 2.10 | N-(2-thiazolyl)-4-hydroxy-2-methyl-2H-1,2-benzthiazine-3-carboxamide-1,1-dioxide or a derivative thereof |
| each of 1.1, 1.2 and 1.7 individually or in any combination | | 2.11 | 6-chloro-5-cyclohexylindane-1-carboxylic acid [(1S)-(+)-isomers or a salt thereof] |
| each of 1.1, 1.2 and 1.7 individually or in any combination | | 2.12 | 3-chloro-4-cyclohexyl-α-methylphenylacetic acid [d(+)-isomers or a salt thereof] |
| each of 1.1 to 1.7 individually or in any combination | | 2.13 | 3-(3-chloro-4-cyclohexylphenyl)-3-methylpropionic acid or a salt thereof |

When the novel composition is in a form suitable for application, for example as bait, the total content of this form of adapted to cause hemorrhagic stomach and/or intestinal lesions. The lethal dose ($LD_{100}$ in the case of a single oral administration) of the combined composition lies, in many cases, between approximately 4 and approximately 25 mg/kg of the body weight for Sprague-Dawley rats; for wild rats (Rattus norvegicus and Rattus rattus) the letal dose lies between approximately 5 and approximately 50 mg/kg of body weight.

Particularly effective representatives of the composition have a lethal dose ($LD_{100}$ in the case of single oral administration) between approximately 4 and aparoximately 10 mg/kg of body weight for Sprague-Dawley rats and between approximately 5 and 20 mg/kg of body weight for wild rats and are therefore from approximately 2 to more than 25 times more effective than commercially-available anticoagulants (in the case of Sprague-Dawley rats and wild rats).

Further active substances, which are optionally incorporated in the compositions, are, e.g., additives which inhibit bacterial vitamin-K-synthesis in the intestine, more particularly sulfonamides, such as 3,4-dimethyl-5-sulfanilamidoisoxazole, N¹-(2-quinoxalinyl)sulfanilamide or 2-sulfanilamido-4-methylpyrimidine; antibiotics and antibacterially-effective substances, such as 5-hydroxytetracycline, penicillin-G, terramycine, chloramphenicol; and other materials antagonistic to vitamin K, such as 2-methoxy-1,4-naphthoquinone, 2,3-dichloro-1,4-naphthoquinone or dihydroxyphenazine-N,N'-dioxide. These active substances are optionally present in the novel compositions in amounts extending from $10^{-4}$ percent by weight to approximately the same amount by weight as components (a) and/or (b).

The new compositions also optionally comprise, as further active substances, one or more compounds with vitamin-D activity, for example ergocalciferol, cholecalciferol or compounds described in Dutch patent specification No. 7,303,068. These active substances are present in the compositions in amounts from zero up to the same amount by weight as anticoagulating agent (a).

Auxiliary substances or adjuvants employed for the production of bait and concentrate are, for example, natural or artificial animal foodstuffs, human foodstuffs, decoy substances, dyes, inert vehicle substances or film-forming adjuvants. Illustrative animal foodstuffs are, for example, maize, corn, fat, fish, meat, bread, rice, seeds, various sorts of flour, such as maize, starch, oat or fish meal, chocolate, cacao powder, sugar or butter. Decoy substances are, for example, sodium glutamate, honey, milk and water and mixtures of these substances. The nature of the dye used is not critical, though blue dyes are regarded as advantageous since they have a particular enticing effect for rats. Inert vehicle substances are, for example, mineral oils, sawdust, talcum, bentonite, pulverized limestone, aluminum oxide or magnesium oxide. Film-forming adjuvants are, for example, polymers which form film coatings which are insoluble in saliva or insoluble in gastric juice. If the new compositions are processed to produce pellets, granules or granular material, conventional pelletizing and granule-forming adjuvants are employed.

The components (a) and (b) are furthermore used for the production of compositions in the form of any desired salt.

From the preceding description one skilled in the art can readily appreciate the nature and scope of the invention, how to prepare suitable compositions and how to use such compositions and the associated process. The following examples are merely illustrative of different aspects of the invention and are in no way limitative thereof.

EXAMPLE 1

Selection of acidic compounds which are suitable as component (b)

Using Sprague-Dawley rats and previously-described testing methods, determine the $LD_5$-values of the following substances:

A. 1-phenyl-3,5-di-(2-thienyl)-4-pyrazole acetic acid
B. 1,5-diphenyl-3-(p-chlorophenyl)-4-pyrazole acetic acid
C. 1,3,5-triphenyl-4-pyrazole acetic acid
D. 1-(p-chlorophenyl)-3,5-di-(2-thienyl)-4-pyrazole acetic acid
E. 1-(p-chlorobenzoyl)-5-methoxy-2-methylindole-3-acetic acid
F. 3-cyclohexyl-1,5-diphenyl-4-pyrazole acetic acid
G. 1,3-diphenyl-5-(p-methoxyphenyl)-4-pyrazole acetic acid
H. 3,5-diphenyl-1-(p-methoxyphenyl)-4-pyrazole acetic acid
I. salicylic acid
K. acetylsalicylic acid
L. N-(2-thiazolyl)-4-hydroxy-2-methyl-2H-1,2-benzothiazine-3-carboxamide-1,1-dioxide
M. 1(o-chlorophenyl)-3,5-(2-thienyl)-4-pyrazole acetic acid
N. d(+)-3-chloro-4-cyclohexyl-α-methyl-phenylacetic acid
O. 1-phenyl-3,5-di-(2-furyl)-4-pyrazole acetic acid
P. 1-methyl-2',4'-difluoroxindole-3-carboxanilide
Q. N-(4-bromophenyl)-3-hydroxy-2-methyl-2H-1,2-benzothiazine-4-carboxamide-1,1-dioxide
R. N-(4-nitrophenyl)-3-hydroxy-2-methyl-2H-1,2-benzothiazine-4-carboxamide-1,1-dioxide Thereafter autopsy the dead animals to determine the cause of death. A single oral dose of any one of compounds (A) to (H) and (L) to (R) in a range extending up to 50 mg/kg of body weight of the rat causes massive hemorrhagic gut lesions before the animal's death. The $LD_5$-value for each of these compounds is below 50 mg/kg of body weight.

The $LD_5$-values for compounds (A), (B), (C) and (D) are less than approximately 5 mg/kg of body weight; for compounds (E), (F), (G), (H), (M) and (N), less than approximately 15 mg/kg of body weight; and for compounds (L), (O), (P), (Q) and (R), less than approx. 50 mg/kg of body weight. The $LD_5$-values for compounds (I) and (K) are far above 100 mg/kg of body weight of the rats. Thereafter compounds (I) and (K) are unsuitable as component (b) for the subject compositions.

This is further confirmed by determining the rodenticidal efficacy of combinations of each of (I) and (K) with anticoagulants. To detect any synergistic rodenticidal action at all, such large amounts of salicylic acid or acetylsalicylic acid has to be used that development of a practical rodenticide based on these components is out of the question.

To investigate rodenticidal efficacy, determine the $LD_{100}$-values for a combination of each of compounds (A) to (H) and (L) to (R) with 2 mg/kg of body weight per rat of 4-hydroxy-2-oxo-3-(1-phenylpropyl)-2H-chromene in accordance with previously specified methods of investigation. Administer each (separately) of compounds (A) to (H) and (L) to (O) and (Q) in sodium-salt form in an aqueous solution in a liquid volume of 5 ml/kg of body weight of the rat and 4-hydroxy-2-oxo-3-(1-phenylpropyl)-2H-chromene suspended in 1 percent tylose (= carboxymethylcellulose) in a liquid volume of 5 ml/kg of body weight of the rat. Administer compounds (P9 and (R) as aqueous suspensions in tylose, each in conjunction with 4-hydroxy-2-oxo-3-(1-phenylpropyl)-2H-chromene, i.e. paralleling the administration of compounds (A) to (H) and (L) to (O).

Note the number of animals which die within 10 days of the respective administrations. Table II shows the results.

Table II shows that component (b) clearly produces a synergistic action with respect to the effect of component (a). The $LD_{100}$-value of 4-hydroxy-2-oxo-3-(1-phenylpropyl)-2H-chromene is 17 mg/kg of body weight for Sprague-Dawley rats.

EXAMPLE 2

Table III shows the mean lethal dose of some anticoagulants or anti-clotting agents along and in combination with 1-phenyl-3,5-di-(2-thienyl)-4-pyrazole acetic acid [component (b)] after a single oral administration to Sprague-Dawley rats.

EXAMPLE 3

Using the methods of investigation of Example 1, administer the following combinations of 4-hydroxy-2-oxo-3-(1-phenylpropyl)-2H-chromene [component (a)] with 1-phenyl-3,5-di-(2-thienyl)-4-pyrazole acetic acid [component (b)] to male and female wild rats (Rattus norvegicus and Rattus ratus) with full stomachs and weighing from approximately 150 to 350 g to obtain the death of 100% of the animals investigated after a single oral dose within a period of investigation of 10 days ($LD_{100}$):

| Component (a) mg/kg of rat body weight | combined with | Component (b) mg/kg of rat body weight |
|---|---|---|
| 45 | | 0 |
| 4 | | 1.5 |
| 3 | | 2 |
| 2 | | 3 |
| 0 | | 7 |

Although component (b) has a high rodenticidal efficacy even when administered alone, its effect is synergistically enhanced by administration in conjunction with component (a). The rodenticidal effect of component (a) is similarly enhanced to an unexpectedly high degree.

Table II

Increase in Rodenticidal Efficacy of 4-hydroxy-2-oxo-3-(1-phenyl-propyl)-2H-chromene (2 mg/kg) by Addition of Component (b) after a Single Oral Dose in Sprague-Dawley Rats

| Component (b) | Dose mg/kg | Number of Animals | % of Animals which Died | LD$_{100}$ (interpolated) |
|---|---|---|---|---|
| A | 0.01 | 40 | 13 | |
| | 0.05 | 20 | 25 | |
| | 0.1 | 30 | 27 | |
| | 0.5 | 60 | 30 | ~2.0 |
| | 1.0 | 60 | 55 | |
| | 1.5 | 44 | 95 | |
| | 2.0 | 44 | 98 | |
| B | 0.05 | 40 | 8 | |
| | 0.1 | 20 | 15 | |
| | 0.2 | 40 | 28 | |
| | 0.5 | 50 | 40 | 1.5 |
| | 1.0 | 70 | 81 | |
| | 1.5 | 40 | 95 | |
| | 2.0 | 20 | 100 | |
| C | 0.5 | 30 | 7 | |
| | 1.0 | 30 | 27 | |
| | 2.0 | 30 | 87 | 3.0 |
| | 3.0 | 20 | 100 | |
| | 5.0 | 10 | 100 | |
| D | 0.1 | 10 | 0 | |
| | 0.2 | 20 | 10 | |
| | 0.5 | 20 | 45 | 5.0 |
| | 2.0 | 20 | 70 | |
| | 5.0 | 10 | 100 | |
| E | 1.0 | 30 | 3 | |
| | 2.0 | 50 | 22 | |
| | 5.0 | 40 | 52 | 7.5 |
| | 7.5 | 40 | 100 | |
| F | 0.5 | 10 | 0 | |
| | 1.0 | 20 | 15 | |
| | 2.0 | 30 | 13 | |
| | 3.5 | 10 | 60 | 7.5 |
| | 5.0 | 20 | 95 | |
| | 7.5 | 10 | 100 | |
| | 10.0 | 30 | 100 | |
| G | 2.0 | 30 | 3 | |
| | 5.0 | 20 | 25 | |
| | 7.5 | 10 | 70 | ~10.0 |
| | 10.0 | 30 | 97 | |
| H | 2.0 | 10 | 20 | |
| | 5.0 | 20 | 40 | ~10.00 |
| | 10.0 | 10 | 100 | |
| L | 2.0 | 20 | 35 | |
| | 5.0 | 20 | 60 | 20.00 |
| | 20.0 | 20 | 100 | |
| M | 2.0 | 10 | 10 | |
| | 5.0 | 20 | 25 | ~10 – 50 |
| | 10.0 | 10 | 80 | |
| N | 1.0 | 20 | 5 | |
| | 2.0 | 30 | 63 | ~ 5 – 10 |
| | 5.0 | 20 | 95 | |
| | 10.0 | 10 | 100 | |
| O | 5.0 | 30 | 7 | |
| | 10.0 | 30 | 17 | ~50 |
| | 20.0 | 20 | 25 | |
| | 50.0 | 20 | 100 | |

Table III

| Component (a) | LD$_{50}$ mg/kg of body weight oral* | | |
|---|---|---|---|
| | Alone | In combination with component (b) | |
| | | 1 mg/kg | 2 mg/kg |
| 4-hydroxy-2-oxo-3-(1-phenyl-propyl)-2H-chromene | 3.0 | 1.7 | 0.55 |
| 4-hydroxy-3-(3-oxo-1-phenyl-butyl)-2H-chromene-2-one | 7.0 | 4 | 0.4 |
| 2-diphenylacetyl-1,3-indandione | 3.5 | 0.5 | 0.3 |
| 2-pivaloyl-1,3-indandione | far above 5 | — | far above 1 |
| 3-(1,2,3,4-tetrahydro-1-naphthyl)-4-oxycoumarin | 4.0 | — | about 0.5 |
| 2-phenylindandione-(1,3) | far above 100 | — | not less than 50 |
| 4-hydroxy-2-oxo-3-[3-oxo-1-(4-nitrophenyl)butyl]-2H-chromene | above 100 | — | 1.3 |

*Ingestion volume: 5 ml/kg, period of observation: 10 days

EXAMPLE 4

Mix 0.05 part by weight of 1-phenyl-3,5-di-(2-thienyl)-4-pyrazole acetic acid with 0.05 part by weight of 4-hydroxy-2-oxo-3-(1-phenylpropyl)-2H-chromene. Finely grind the resulting admixture and suspend the thus-obtained ground material in 4.9 parts by weight of molten mutton suet. Homogeneously mix the produced suspension with 95 parts by weight of oat flakes. Use a high speed cutter as a mixing machine to obtain a highly effective ready-to-use rodenticide.

Instead of 4-hydroxy-23-(1-phenylpropyl)-2H-chromene similarly process each of 4-hydroxy-2-oxo-3-(3-oxo-1-phenylbutyl)-2H-chromene, 2-di-phenylacetyl-indandione-(1,3) and 3-(1,2,3,4-tetrahydro-1-naphthyl)-4-oxycoumarin in the same quantity ratios to produce effective rodenticides ready for use.

EXAMPLE 5

Mix 0.5 part by weight of 1-phenyl-3,5-di-(2-thienyl)-4-pyrazole acetic acid with 0.5 part by weight of 4-hydroxy-2-oxo-3-(1-phenylpropyl)-2H-chromene. Grind the obtained admixture finely and then suspend it in 4.0 parts by weight of a triglyceride mixture of saturated plant fatty acids with $C_8$, $C_{10}$ and $C_{12}$ (see H. P. Fielder, "Lexikon der Hilfsstoffe fur Pharmazie, Kosmetik und angrenzende Gebiete", Editio Cantor KG., Aulendorf in Wurttemberg, 1971, page 383, column 2, 4th title). Homogeneously mix the resulting suspension with 95 parts by weight of maize meal in a mixing or kneading machine to obtain a rodenticide concentrate. Add the concentrate to animal feeds in a weight ratio between 1 to 5 and 1 to 10.

Replacing 1-phenyl-3,5-di-(2-thienyl)-4-pyrazole acetic acid with 1,5-diphenyl-3-(p-chlorophenyl)-4-pyrazole acetic acid in the same weight ratios and processing same with 4-hydroxy-2-oxo-3-(1-phenylpropyl)-2H-chromene yield an extremely effective and similarly useful rodenticide concentrate.

EXAMPLE 6

Suspend 0.05 part by weight of 1-(p-chlorobenzoyl)-5-methoxy-2-methylindole-3-acetic acid and 0.05 part by weight of 4-hydroxy-2-oxo-3-(1-phenylpropyl)-2H-chromene in 4.9 parts by weight of liquid paraffin. Homogeneously mix the resulting suspension with 5 parts by weight of cane sugar and 90 parts by weight of oat flakes to obtain an effective ready-to-use rodenticide.

EXAMPLE 7

Homogeneously mix 0.5 parts by weight of 1-(p-chlorobenzoyl)-5-methoxy-2-methylindole-3-acetic acid and 0.5 by weight of 4-hydroxy-2-oxo-3-(1-phenylpropyl)-2H-chromene with one part by weight of sodium glutamate and 93 parts by weight of maize meal. Then mix the resulting admixture with a solution of 5 parts by weight of gum arabic in 20 parts by weight of water.

Press part of the thus-produced moist-powder mixture through a granulating sieve with 1.8 mm mesh-clearance width and dry the obtained moist granulate at 40° C in a hurdle-type drying cupboard or in a fluidized bed to obtain a particularly effective rodenticide.

Process the remaining part of the moist-powder mixture to form pellets in accordance with the Merumeriza method, the pellets having a diameter of from 1.2 to 1.6 mm. They constitute a rodenticide which is readily consumed by rats.

Pellets are similarly prepared A) with the 1-(p-chlorophenyl)-5-methoxy-2-methylindole-3-acetic acid as the sole actice ingredient and B) with the 4-hydroxy-2-oxo-3-(1-phenylpropyl)-2H-chromene as the sole active ingredient. Such pellets are then either mixed together or made available (separately) to rodents.

EXAMPLE 8

Mix 0.05 part by weight of 1,5-diphenyl-3-(p-chlorophenyl)-4-pyrazole acetic acid with 0.05 part by weight of 4-hydroxy-2-oxo-3-(1-phenylpropyl)-2H-chromene. Finely grind the resulting admixture and suspend it in 4.9 parts byweight of molten mutton suet. Homogeneously mix the thus-obtained suspension with 95 parts by weight of oat flakes in a high-speed cutting machine. The thus-prepared mixture is a highly-effective ready-to-use rodenticide.

Similarly process 4-hydroxy-2-oxo-3-(3-oxo-1-phenylbutyl)-2H-chromene, 2-diphenylacetylindandione-(1,3) or 3-(1,2,3,4-tetrahydro-1-naphthyl)-4-oxycoumarin (in the place of the 4-hydroxy-2-oxo-3-(1-phenylpropyl)-2H-chromene) with the same quantity ratios to form an effective ready-to-use rodenticide.

EXAMPLE 9

Mix and then finely grind 0.4 part by weight of 1,5-diphenyl-3-(p-chlorophenyl)-4-pyrazole acetic acid with 0.6 part by weight of 4-hydroxy-2-oxo-3-(1-phenylpropyl)-2H-chromene before suspending the resulting ground admixture in 4.0 parts by weight of a triglyceride mixture of saturated plant fatty acids with $C_8$, $C_{10}$ and $C_{12}$ (see H. P. Fielder, "Lexikon der Hilfsstoffe fuer Pharmazie, Kosmetik und angrenzende Gebiete", Editio Cantor KG., Aulendorf in Wurttemberg, 1971, page 382, column 2, 4th title). Mix the thus-prepared suspension homogeneously with 95 parts by weight of maize meal in a mixing or kneading machine. The obtained mixture is a concentrate form of rodenticide. Add it to animal feed in a weight ratio lying between 1 to 5 and 1 to 10 and make the thus-treated animal feed available to undesired rodents.

Replace the 1,5-diphenyl-3-(p-chlorophenyl)-4-pyrazole acetic acid with 1-(o-chlorophenyl)-3,5-[di-(2-thienyl)]-4-pyrazole acetic acid (in the same amount by weight) and process with 4-hydroxy-2-oxo-3-(1-phenylpropyl)-2H-chromene to form an extremely effective rodenticide concentrate.

EXAMPLE 10

Suspend 0.07 part by weight of 1-(p-chlorobenzoyl)-5-methoxy-2-methylindole-3-acetic acid and 0.03 part by weight of 4-hydroxy-2-oxo-3-(1-phenylpropyl)-2H-chromene in 4.9 parts by weight of liquid paraffin. Homogeneously mix the resulting suspension with 5 parts by weight of cane sugar and 90 parts by weight of oat flakes to obtain an effective ready-to-use rodenticide.

EXAMPLE 11

Homogeneously mix 0.6 part by weight of 1,5-diphenyl-3-(p-chlorophenyl)-4-pyrazole acetic acid and 0.4 part by weight of 4-hydroxy-2-oxo-3-(1-phenylpropyl)-2-H-chromene with one part by weight of sodium glutamate and 93 parts by weight of maize meal. Thoroughly moisten the resulting admixture with a solution of 5 parts by weight of gum arabic in 20 parts by weight of water.

Force part of the moistened-powder mixture through a granulating sieve with a clearance mesh width of 1.8 mm, and dry the thus-prepared moist granulate at 40° C in a hurdle-type drying cupboard or in a fluidized bed. The produced granulate constitutes a particularly-effective rodenticide.

Process the remaining part of the moistened powder mixture according to the Merumeriza method to form pellets with diameters of from 1.2 to 1.6 mm. These pellets constitute a ready-to-use rodenticide which is readily consumed by rats.

EXAMPLE 12

Following the rules for the examination of rodenticides against rats and mice (edited by Bundesgeshundheitsamt, Institut fuer Wasser-, Boden- und Lufthygiene, Biologische Bundesanstalt fur Land- und Forstwirtschaft, Staatliches Medizinaluntersuchungsamt, Abt. fuer hygienische Schädlingsbekampfung), female Sprague-Dawley rats weighing about 200 grams, kept in single boxes, were provided with the rodenticidal active substances* alone or in combination (expressed in mg/kg) in 4 grams of bait per rat, i.e. 20 g of bait/kg of body weight. These soft consistent, i.e. not crumbly, baits were prepared from Semmelmehl (i.e. powder prepared by grinding dry white bread) and some water. The rats on an empty stomach were provided with these baits as the only food during one day, tap water was ad libitum.

* 4-hydroxy-2-oxo-3-(3-oxo-1-phenyl-butyl)-2H-chromene and 1,5-diphenyl-3-(p-chlorophenyl)-4-pyrazole acetic acid The baits containing the active substances were well accepted by the rats in any case, that means, the baits were completely consumed. Thereafter, the animals were provided with usual standard diet Atromine R for the remaining duration of the test.

The mortality rate was determined during a test period of 10 days. From Table IV follows, that the rodenticidal activity of component $a$, e.g. component 1.2 of table I, is amplified by the component $b$, e.g. component B of example 1, that means, that component $b$ has an synergistic influence on component $a$.

Another advantage of the combination of $a$ and $b$ is, that its administration (e.g. of component 1.2 and component) results in a quicker death of the rats than the sole administration of component 1.2.

The invention and its advantages are clearly portrayed in and understood from the foregoing description. It is apparent that various changes may be made in the compositions, their preparation and their application without departing from the spirit or scope of the invention or sacrificing its material advantages.

What is claimed is:

1. A composition which comprises (a) component means to inhibit mammalian blood clotting and (b) component means to produce hemorrhagic alimentary canal lesions when administered in a single oral dose of less than 50 mg/kg of body weight to a Sprague-Dawley rat with an empty stomach, the composition containing component means (a) and component means (b) in a combined concentration of more than $10^{-3}$ percent by weight based on the total weight of the composition.

2. A composition according to claim 1 wherein component means $b$ produces hemorrhagic gut and/or stomach lesions in a Sprague-Dawley rate with an empty stomach when administered thereto in a single oral dose of less than 15 mg/kg of body weight.

3. A composition according to claim 2 wherein component means $b$ produces hemorrhagic gut and/or stomach lesions in a Sprague-Dawley rat with an empty stomach when administered thereto in a single oral dose of less than 5 mg/kg of body weight.

4. An admixture of component means $a$ and component means $b$ according to claim 1.

5. A composition according to claim 1 wherein the weight ratio of component means $a$ to component means $b$ is from (5 to 95)/(95 to 5), the composition containing component means $a$ and component means $b$ in a combined concentration of more than $10^{-2}$ percent by weight based on the total weight of the composition.

6. A solid-form composition according to claim 1.

7. A composition according to claim 1 wherein the combined content of component means $a$ and component means $b$ is about 5 percent by weight.

8. A composition according to claim 1 wherein component means $a$ is structurally related to at least one member selected from the group consisting of 1,3-indandione, coumarin, 2-azacycloalkylmethyl-substituted benzyhydryl-ketone and 2-azacycloalkylmethyl-substituted benzhydryl-carbinol and their salts.

9. A composition according to claim 1 wherein component means $b$ is a member selected from the group Table IV

| | Component 1.2 100 mg/kg | Component 1.2 200 mg/kg | Component 1.2 3 mg/kg + Component B 1.5 mg/kg | Component 1.2 4 mg/kg + Component B 1 mg/kg |
|---|---|---|---|---|
| % of Animals which Died | 80 | 80 | 100 | 100 |

Throughout the preceding disclosure, including the specific examples, each anticoagulant (or blood-clot inhibitor) is readily replaced by any other one or combination of noted anticoagulants, and each hemorrhagic-lesion-producing component is similarly replaced by any other one or combination of noted components which produce hemorrhagic lesions in the alimentary canal when a single oral dose of less than 50 mg/kg of body weight is ingested by Sprague-Dawley rats with empty stomachs.

consisting of (1) an acidic carbocyclic or heterocyclic aromatic compound with a molecular weight within the range of from approximately 200 to approximately 500, with from 1 to 5 rings and from 6 to 30 carbon atoms and with a $pK_A$-value of from 1.5 to 5.5 and (2) a precursor of (1) which releases (1) or yields (1) in the pH range of mammalian gastric juice.

10. A composition according to claim 9 wherein (1) has a $pK_A$-value of from 2 to 5 and (2) is a salt or a derivative of (1).

11. A composition according to claim 9 wherein (1) is a compound having a

group, the carbon atom of which is separated by at least two carbon-to-carbon single bonds from any C=C-double bond and is directly linked through from 1 to 3 carbon atoms to an aromatic carbocyclic- or heterocyclic-ring carbon atom.

12. A composition according to claim 9 which contains at least one gut- and/or stomach-lesion-producing component selected from the group consisting of (I) an arylacetic acid, (II) a heteroaryl-acetic acid and (III) a salt of one of (I) and (II).

13. A composition according to claim 9 which contains at least one gut- and/or stomach-lesion-producing component selected from the group consisting of (I') an α-aryl-α-methylacetic acid, (II') a α-heteroaryl-α-methylacetic acid and (III') a salt of one of (I') and (II').

14. A composition according to claim 9 which contains at least one gut- and/or stomach-lesion-producing component selected from the group consisting of (I'') an arylpropionic acid, (II'') a heteroaryl-propionic acid and (III'') a salt of one of (I'') and (II'').

15. A composition according to claim 9 wherein component $b$ is at least one acidic enol with the conjugated system

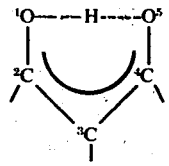

or a salt thereof.

16. A composition according to claim 1 which comprises at least one member selected from the group consisting of active compound means for inhibiting bacterial vitamin-K synthesis in the intestine and compound means with vitamin-D activity.

17. A composition according to claim 1 having components $a$ and $b$ in a rodenticidally-effective ratio and the composite of components $a$ and $b$ in a rodenticidally-effective concentration.

18. A rodent-combatting method which comprises making accessible thereto a composition according to claim 1.

19. A compositon according to claim 1 wherein component means $a$ is 4-hydroxy-2-oxo-3-(3-oxo-1-phenylbutyl)-2H-chromene and component means $b$ is 1,5-diphenyl-3-(p-chlorophenyl)-4-pyrazole acetic acid.

20. A rodent-combatting method which comprises making accessible to at least one rodent, either concurrently or sequentially, component means to cause hemorrhagic alimentary canal lesions and component means to inhibit or prevent blood clotting.

21. Rodenticide in pellet form, each pellet of which has a core encased in a casing which is soluble in intestinal juice, but not in gastric juice, the casing bearing an emetic-containing coating and an outermost layer; the core being composed of a rodenticidally-effective composition, emetic in the emetic-containing coating being in a sufficient amount to effect emesis in a human or in a domestic animal upon ingestion of the pellet, and the outermost layer being insoluble in saliva, but soluble in gastric juice.

22. Pellet-form rodenticide according to claim 21 wherein the rodenticidally-effective composition is a composition which comprises (a) component means to inhibit mammalian blood clotting and (b) component means to produce hemorrhagic alimentary canal lesions when administered in a single oral dose of less than 50 mg/kg of body weight to a Sprague-Dawley rat with an empty stomach, the composition containing component means $a$ and component means $b$ in a combined concentration of more than $10^{-3}$ percent by weight based on the total weight of the composition.

* * * * *

UNITED STATES PATENT OFFICE
CERTIFICATE OF CORRECTION

Patent No. 4,011,332                    Dated March 8, 1977

Inventor(s)    Schoetensack et al

It is certified that error appears in the above-identified patent and that said Letters Patent are hereby corrected as shown below:

Column 3, line 65, to column 5, line 38, "1,3-indandione...Hungar.," should read --1,3-indandione [cf. J. Organ. Chem., 25, 1860 (1962)], 2-phenyl-1,3-indandione [Chem.Ber. 47, 1439 (1914)], 2-(p-chlorphenyl)-1,3-indandione (British patent No. 748,251), 2-(α,α,α-trifluoro-p-tolyl)-1,3-indandione (Dutch Octrooischrift No. 65 11 171), 2-(p-bromophenyl)-1,3-indandione (USP 2,847,747), 2-(p-methoxyphenyl)-1,3-indandione (USP 2,899,358), 2-(diphenylacetyl)-1,3-indandione (USP 2,672,483), 2-[1-(p-bromophenyl)-1-phenyl]acetyl-1,3-indandione (French patent No. 1,269,638), 2-[1-(p-tolyl)-1-phenyl]acetyl-1,3-indandione (Russian patent No. 145,417), 2-phenyl-2-morpholinomethyl-1,3-indandione (German patent No. 1,919,895), 2-hydroxymethyl-2-phenyl-1,3-indandione [Comp. Rend., 257(4), 933-6 (1963)], 2-(1-naphthyl)-1,3-indandione (French patent No. 1,085,097), 2-[α-(p-ethylphenacetyl)benzyl]-1,3-indandione (Zh. Obshch. Khim., 35(1), 184-5 (1965)] and 2-pivaloyl-1,3-indandione [Ind. Eng. Chem., 34, 494-7 (1941)] and their salts.

Preferred anti-clotting agents or anticoagulants based on coumarin are: 4-hydroxy-2-oxo-3-(1-phenylpropyl)-2H-chromene (USP 2,723,276), 4-hydroxy-2-oxo-3-(3-oxo-1-phenylbutyl)-2H-chromene (USP 2,427,578) and its sodium salt (USP 2,765,321), 4-hydroxy-2-oxo-3-[3-oxo-1-(p-chlorophenyl)butyl]-2H-chromene (USP 2,648,682), 2-methoxy-5-oxo-2-methyl-4-phenyl-3,4-dihydro-2H,5H-pyrano[3,2-c][1]benzopyrane[cf. J. Am. Chem. Soc., 66, 902-6 (1944)], 4-hydroxy-2-oxo-3-[4-hydroxy-2-oxo-2H-chromenyl-(3)-methyl]-2H-chromene [Arquiv. inst. biol. (Sao Paulo), 14, 293-303 (1943)], 4-hydroxy-2-oxo-3-{1-[4-hydroxy-2-oxo-2H-chromenyl-(3)]-ethyl}-2H-chromene (Czech. patent No. 85,918), 4-hydroxy-2-oxo-3-{2-methoxy-1-[4-hydroxy-2-oxo-2H-chromenyl-(3)]-ethyl}-2H-chromene [Rec. Trav. Chim. 72, 358-364 (1953)], 4-hydroxy-2-oxo-3-{3-methylmercapto-1-[4-hydroxy-2-oxo-2H-chromenyl-(3)]-propyl}-2H-chromene [Proc. Intern. Conf. Thrombosis and Embolism, 1st, Basle, 1954, 223-7 (published 1955)], ethyl-bis-[4-hydroxy-2-oxo-2H-chromenyl-(3)]-acetate (USP 2,482,510), 3-(1,2,3,4-tetrahydro-1-naphthyl)-4-oxycoumarin (German patent No. 1,014,551), 3-[α-(2-furyl)-β-acetylethyl]-4-oxycoumarin (German patent No. 947,164), 4-hydroxycoumarin-3-carboxylic acid-β-diethylaminoethylamide (French patent No.

UNITED STATES PATENT OFFICE
CERTIFICATE OF CORRECTION

Patent No. 4,011,332         Dated   March 8, 1977

Inventor(s)   Schoetensack et al

It is certified that error appears in the above-identified patent and that said Letters Patent are hereby corrected as shown below:

1,369,991), 4-hydroxy-3-(3,5-xylyl)coumarin [Sci. Communs. Research Dept., N.V. Koninkl. Pharm. Fabrieken v/h *Brocades-Stheeman & Pharmacia*, 10, 7-78 (1960-1961)], 3-[1-(p-chlorophenyl)propyl]-4-hydroxycoumarin (British patent No. 734,823), 3-(1-naphthyl)-4-hydroxycoumarin (USP 2,723,276), 3-[1-(p-iodophenyl)-3-oxobutyl]-4-hydroxycoumarin (Belgian patent No. 626,118), 4-hydroxy-3-[1-(p-nitrophenyl)-3-oxopentyl]coumarin (USP 2,648,682) and 4-hydroxy-3-(3-oxo-1-phenylpentyl)coumarin [*Izv. Vysshikh Uchebn. Zavedenii*, Khim. Tekhnol., 5(1), 107-111 (1962)].

Further anti-clotting agents include the following 2-azacycloalkylmethyl-substituted benzhydrylketones and -carbinols: 1-phenyl-3-(2-piperidyl)-1-(p-tolyl)-2-propanone; 3,3-diphenyl-1-(2-pyrrolidinyl)-2-pentanone; 1,1-diphenyl-3-[2-(hexahydro-1H-azepinyl)]-2-propanone; 1-(4-fluorophenyl)-1-phenyl-3-(2-piperidyl)-2-propanone; 1-(4-methylthiophenyl)-1-phenyl-3-(5,5-dimethyl-2-pyrrolidinyl)-2-propanone; 1-(p-coumenyl)-1-phenyl-3-(4-*tert.*-butyl-2-piperidinyl)-2-propanone; 3,3-diphenyl-1-[2-(hexahydro-1H-azepinyl)]-2-butanone; 3-(2,4-dichlorophenyl)-3-phenyl-1-(2-piperidyl)-2-heptanone; 1,1-diphenyl-3-(5-methyl-2-pyrrolidinyl)-2-propanone; 3,3-diphenyl-1-(2-piperidyl)-2-butanone; α-(α-methyl-α-phenylbenzyl)-2-piperidinethanol; α-(α-ethyl-α-phenylbenzyl)-2-pyrrolidinethanol; 2-(2,5-dimethyl-α-phenylbenzyl)-2-piperidinethanol and α-(diphenylmethyl)-2-(hexahydro-1H-azepin)ethanol  and their salts, which are described in the German patent specification 2,417,783, and 4'-(fluorophenyl)-2-(2-pyrrolidinyl)acetophenone, 4'-phenyl-2-(5,5-dimethyl-2-pyrrolidinyl)acetophenone, 4'[p-(trifluoromethyl)phenyl]-2-(2-piperidyl)acetophenone, 4'-(p-butoxyphenyl)-2-(4-*tert.*-butyl-2-piperidyl)acetophenone, 2'-phenoxy-2-(2-piperidyl)acetophenone, 4'-(p-fluorophenoxy)-2-(5,5-dimethyl-2-pyrrolidinyl)acetophenone, 4'-(p-chlorophenoxy)-2-(2-piperidyl)acetophenone, 4'-[m-(trifluoromethyl)phenoxy]-2-(2-piperidyl)acetophenone, 4'-(p-butoxyphenoxy)-2-(2-pyrrolidinyl)acetophenone, 2-(2-piperidyl)-4'-(trans-p-tolylvinylene)acetophenone, 2-(2-hexahydro-1H-azepinyl)-4'-(trans-styryl)acetophenone, 4'-(m-methoxy-phenylvinylene)-2-(2-pyrrolidinyl)acetophenone, 2-(2-piperidyl)-4'-[(p-methylthio)phenylvinylene]acetophenone, 4'-(3-phenoxypropoxy)-2-(2-

UNITED STATES PATENT OFFICE
CERTIFICATE OF CORRECTION

Patent No. 4,011,332           Dated  March 8, 1977

Inventor(s)  Shoetensack et al

It is certified that error appears in the above-identified patent and that said Letters Patent are hereby corrected as shown below:

piperidyl)acetophenone, 4'-(4-phenylbutyl)-2-(2-piperidyl)acetophenone, 4'-(α,α-dimethylbenzyl)-2-(piperidyl)acetophenone, 4'-phenethyl-2-(3,5-diethyl-2-piperidyl)acetophenone, 4'-phenyl-2-(2-pyrrolidinyl)acetophenone, α-[2-(2-phenylethoxy)phenyl]-2-piperidinethanol, α-(p-phenoxyphenyl-2-pyrrolidinethanol, α-[4-(4-bromophenoxy)phenyl]-6-methyl-2-piperidinethanol, α-(p-phenethyl)phenyl-2-pyrrolidinethanol, α-(p-biphenyl)-2-hexahydro-1H-azepinethanol, α-[3-(4-phenoxybutoxy)phenyl]-2-piperidinethanol, and α-(4-benzyl)phenyl-2-piperidinethanol and their salts, which are described in German patent specification 2,418,480.

The following rare earth metal salts are, alternatively, used as anticlotting agents: dineodymiumdihydroxybenzene disulfonate (*Acta physiol. Acad. Sci. Hungar.*,--.  Column 5, line 62, "European J. Pharmacol., 22," should read --*European J. Pharmacol., 22,*--.  Column 6, lines 1 and 2, "J. Pharmacol. exp., 96," should read --*J. Pharmacol. exp., 96,*--; line 37, "p" should read --*p*--; line 38, "indometacine" should read --indomethacine--; line 50, "J. Am. Chem. Soc., 87," should read --*J. Am. Chem. Soc., 87,*--.  Column 8, line 4, "n" should read --an--; line 53, "p-methoxyphenyl" should read --*p*-methoxyphenyl--; line 55, "p-chlorophenyl" should read --*p*-chlorophenyl--; line 59, "p-chlorobenzoyl" should read --*p*-chlorobenzoyl--; line 67, "(p-chlorophenyl)3,5" should read --(*p*-chlorophenyl)-3,5--.  Column 9, lines 1, 5, 7, 24, 26 and 28, "p-" should read -- *p*- --; line 30, "O" should read --*o*--; line 31, "h" should read --*H*--; lines 37, 39, 42, 43, 45, 47, 53, 55, 57 and 60, "H" should read --*H*--.  Column 10, lines 1 through 9, "J. Med. Chem., ... (1971), J. Med. Chem., 16," should read --*J. Med. Chem., 15,* 1297-1306 (1972), *Angew. Chem., 84,* 512-526 (1972), South African patent No. 7201706, Belgian patent No. 704,182, *J. Med. Chem., 16,* 490-493 (1973), German Offenlegungsschrift No. 2,143,600, Belgian patent No. 633,134, *J. Med. Chem., 16,* 172-174 (1973), *J. Med. Chem. 16,* 493-96 (1973), *J. Med. Chem., 14,* 973-977 (1971), *Compt. Rend.,* Ser. D, *273,* 911 (1971), *J. Med. Chem., 16,*--; lines 33 and 37, "H" should read --*H*--; line 55, "metls" should read --metals--.  Column 13, at approximately lines 6, 8 and 11 in the definition of Component (a) "H" should read --*H*--; at approximately lines 5, 18,

UNITED STATES PATENT OFFICE
CERTIFICATE OF CORRECTION

Patent No. 4,011,332           Dated March 8, 1977

Inventor(s) Schoetensack et al

It is certified that error appears in the above-identified patent and that said Letters Patent are hereby corrected as shown below:

20, 25 and 27 in the definition of Component (b), "p-" should read --$p$- --; at approximately line 30 in the definition of Component (b), "H" should read --$H$--; lines 41 to 43, "When...adapted" should read --adapted--; line 54, "apparox-" should read --approx- --. Column 15, lines 35, 38 and 40, "p-" should read --$p$- --; lines 44, 52 and 54, "H" should read --$H$--; line 46, "o-chlorophenyl)-3,5-" should read --$o$-chlorophenyl)-3,5-di- --. Column 16, lines 15, 21, 26, 35 and 48, "H" should read --$H$--; line 22, "tylose" should read --Tylose--; line 24, "(P9" should read --(P)--. Column 18, at approximately lines 5, 57, 59 and 64, "H" should read --$H$--. Column 19, lines 5, 12, 14, 22, 39, 44 and 56 (each occurence) "H" should read --$H$--; line 12, "23" should read --2-oxo-3--; lines 35, 42 and 53, "p-" should read --$p$- --. Column 20, lines 3, 30, 45, 53 and 64, "p-" should read --$p$- --; line 5, "actice" should read --active--; lines 6, 14, 22, 25, 32, 49, 55 and 66, "H" should read --$H$--; line 46, "o-" should read --$o$- --. Column 21, line 32, "H" should read --$H$--; line 47, "ponent)" should read --ponent B)--. Column 22, lines 18, 23, 28, 31, 33, 39 and 47, "$b$" should read --(b)--; line 19, "rate" should read --rat--; lines 27, 30, 38, and 41, "$a$" should read --(a)--. Column 23, line 31 (claim 15, line 21), "$b$" should read --(b)--. Column 24, lines 7 and 8, "$a$ and $b$" should read --(a) and (b)--; line 14, " " should read --(a)--; line 15, "H" should read --$H$-- and "$b$" should read --(b)--; line 16, "p-" should read --$p$- --.

Signed and Sealed this

Thirteenth Day of December 1977

[SEAL]

Attest:

RUTH C. MASON           LUTRELLE F. PARKER
Attesting Officer          Acting Commissioner of Patents and Trademarks